US008502982B2

(12) United States Patent
Mace et al.

(10) Patent No.: US 8,502,982 B2
(45) Date of Patent: Aug. 6, 2013

(54) FLOW CELL AND SYSTEM FOR DETECTION OF TARGET IN AQUEOUS ENVIRONMENT USING ARRAYED IMAGING REFLECTOMETRY

(75) Inventors: Charles R. Mace, Auburn, NY (US);
Benjamin L. Miller, Penfield, NY (US);
Lewis J. Rothberg, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/261,818

(22) Filed: Oct. 30, 2008

(65) Prior Publication Data

US 2009/0153867 A1   Jun. 18, 2009

Related U.S. Application Data

(60) Provisional application No. 60/983,742, filed on Oct. 30, 2007.

(51) Int. Cl.
*G01N 21/55* (2006.01)
*G01B 9/02* (2006.01)

(52) U.S. Cl.
USPC ............ 356/445; 356/246; 356/369; 356/504

(58) Field of Classification Search
USPC ................... 356/445–448, 244, 246, 73, 504, 356/632, 450, 491–495, 364–369
See application file for complete search history.

(56) References Cited

U.S. PATENT DOCUMENTS

| | | | |
|---|---|---|---|
| 5,578,832 A | 11/1996 | Trulson et al. | |
| 5,869,272 A | 2/1999 | Bogart et al. | |
| 6,611,634 B2 | 8/2003 | Herron et al. | |
| 7,292,349 B2 | 11/2007 | Miller et al. | |
| 7,551,294 B2 * | 6/2009 | Rothberg | 356/504 |
| 2003/0112446 A1 * | 6/2003 | Miller et al. | 356/504 |
| 2003/0148391 A1 * | 8/2003 | Salafsky | 435/7.2 |
| 2005/0214167 A1 * | 9/2005 | Archibald et al. | 422/68.1 |
| 2006/0269930 A1 | 11/2006 | Robotti et al. | |
| 2007/0076214 A1 | 4/2007 | Rothberg et al. | |
| 2009/0275016 A1 * | 11/2009 | Miller et al. | 435/5 |
| 2010/0075300 A1 * | 3/2010 | Miller et al. | 435/5 |
| 2011/0275532 A1 * | 11/2011 | Mace et al. | 506/9 |

OTHER PUBLICATIONS

Baggio et al, "Induced Fit of an Epitope Peptide to a Monoclonal Antibody Probed with a Novel Parallel Surface Plasmon Resonance Assay", Feb. 11, 2005, The Journal of Biological Chemistry, vol. 280, No. 6, pp. 4188-4194.*
Gao et al., "Biomolecular Sensing Using Near-Null Single Wavelength Arrayed Imaging Reflectometry," Analytical Chemistry 78(18):6622-7 (2006).
International Search Report for International Patent Application No. PCT/US08/81804 (Apr. 22, 2009).
Written Opinion of the International Searching Authority for International Patent Application No. PCT/US08/81804 (Apr. 9, 2009).
Gao et al., "Label-Free Sensing of Binding to Microarrays Using Brewster Angle Straddle Interferometry," Anal. Chem. 79:7589-7595 (2007).
Lu et al., "Reflective Interferometric Detection of Label-Free Oligonucleotides," Anal. Chem. 76:4416-4420 (2004).

* cited by examiner

*Primary Examiner* — Hoa Pham
(74) *Attorney, Agent, or Firm* — LeClairRyan, a Professional Corporation

(57) ABSTRACT

A flow cell for use in an arrayed imaging reflectometry detection system is described herein. The flow cell includes: first and second members that are secured together to define a substantially fluid-tight chamber having an inlet and an outlet, at least the second member being light transmissive; and a chip having a substrate, one or more coating layers on the substrate, and one or more probe molecules tethered to the outermost coating layer, the chip being positioned with the outermost coating layer and the one or more probe molecules thereon exposed to fluid in the chamber and facing the second member, whereby light passing through the second member is reflected by the chip.

26 Claims, 9 Drawing Sheets

FLOW CELL AND SYSTEM FOR DETECTION OF TARGET IN AQUEOUS ENVIRONMENT USING ARRAYED IMAGING REFLECTOMETRY

This application claims the priority benefit of U.S. Provisional Patent Application Ser. No. 60/983,742, filed Oct. 30, 2007, which is hereby incorporated by reference in its entirety.

STATEMENT OF GOVERNMENT SPONSORSHIP

This invention was made with government support under grant number R24-AL054953 awarded by the National Institutes of Health. The government has certain rights in this invention.

FIELD OF THE INVENTION

This invention relates to a flow cell and system designed for arrayed imaging reflectometry ("AIR"), and specifically for the detection of target molecules in an aqueous environment.

BACKGROUND OF THE INVENTION

The principle of AIR is described in co-pending U.S. patent application Ser. No. 10/282,274, filed Oct. 28, 2002, now U.S. Pat. No. 7,292,349, issued Nov. 6, 2007. AIR exploits interference between reflections from the medium/coating and coating/substrate interfaces, exhibiting changes in reflectivity upon binding of biomolecules to the coating. In practice, using a silicon wafer having an oxide coating, judicious choice of incident angle and wavelength can be used with s-polarized light to obtain near complete destructive interference (i.e., reflectivity that is preferably less than about $10^{-5}$ or $10^{-6}$ under some circumstances) in the absence of a target molecule. The condition of near complete (or near perfect) destructive interference is removed upon target molecule binding. Thus, highly sensitive detection of even small quantities of a target molecule is possible.

While AIR using s-polarized light has proven to be a highly sensitive, simple analytical method for the quantitative detection of a variety of biomolecular analytes, it is much more easily carried out in a dry state, that is, with an air/oxide interface rather than with an aqueous/oxide interface. This is a consequence of the difference in the refractive indexes of the media (water≈1.33; air≈1), and the difference in incidence angles that are required to achieve the condition of near complete destructive interference in these media. Using silicon/oxide as the substrate/coating system, in air this angle is about 70.5 degrees whereas in water this angle is about 85.5. The system that has proven to be optimal in air, however, could not be optimized for use in aqueous environments.

There is a need for obtaining an AIR system that is operable in aqueous environments yet maintains the sensitivity of the AIR system that is optimal for "dry" state described above. Detection in aqueous environments is preferred for most biological targets, because the aqueous condition more accurately replicates that condition under which the target molecule normally exists. This is also believed to improve protein viability, as well as allow for different types of measurements such as the acquisition of kinetic information (e.g., on/off rates for coupling to a probe, comparative affinity between two different target molecules, etc.) and even continuous flow for real-time sensors. There exists a substantial need, therefore, for an improved AIR system that is capable of achieving these results.

The present invention is directed to overcoming these and other deficiencies in the art.

SUMMARY OF THE INVENTION

A first aspect of the present invention relates to a flow cell for use in an arrayed imaging reflectometry detection system. The flow cell of the present invention includes: first and second members that are secured together to define a substantially fluid-tight chamber having an inlet and an outlet, at least the second member being light transmissive; and a chip having a substrate, one or more coating layers on the substrate, and one or more probe molecules tethered to the outermost coating layer, the chip being positioned with the outermost coating layer and the one or more probe molecules thereon exposed to fluid in the chamber and facing the second member, whereby light passing through the second member is reflected by the chip.

According to one preferred embodiment, the chip utilized in the flow cell comprises one or more coating layers that are suitably dimensioned to afford near complete destructive interference of reflected light when s-polarized light of an appropriate incident angle passes through the second member and reflects from the chip surface.

According to another preferred embodiment, the chip utilized in the flow cell comprises two or more coating layers that are suitably dimensioned to afford near complete destructive interference of reflected light when s-polarized light of an appropriate incident angle passes through the second member and reflects from the chip surface.

A second aspect of the present invention relates to a detection system that includes a flow cell according to the first aspect of the present invention, wherein the one or more probe molecules specifically bind to one or more target molecules; a fluid sample source in fluid communication with the inlet of the flow cell; a light source that is positioned to illuminate the chip; and a detector that is positioned to detect light reflected from the surface of the chip, wherein the angle of incidence of the illuminating light is suitable to produce a condition of near perfect destructive interference in the absence of the one or more target molecules and a substantial change in light reflectivity in the presence of the one or more target molecules.

A third aspect of the present invention relates to a method for sensing at least one target. This method is carried out by providing a detection system according to the second aspect of the invention; directing a light at the front and back surfaces of the coating on the chip in a manner effective to result in a condition of near perfect destructive interference; introducing a fluid sample into the flow cell; measuring light reflected from the chip; and providing an output identifying the at least one target based on the measured reflected light.

The present invention improves upon prior arrayed imaging reflectometry (AIR) by affording a system that is designed to operate with aqueous detection environments (which maintains biological activity) while achieving sensitivity previously attained only with "dry" AIR systems. Using a preferred system, ΔR/R values of approximately 41,500% and 560% for binding one nanometer and one Angstrom, respectively, should be readily achieved. Moreover, target molecules that cause sub-Angstrom level changes in thickness are sufficient for detection using a system of this present invention. This new form of "wet" AIR permits measurement of binding kinetics (on/off rates) for an array of analytes, as well as permits continuous-flow time resolved measurements of analytes in solutions. These types of measurements were not possible with prior "dry" AIR systems.

BRIEF DESCRIPTION OF THE DRAWINGS

In FIG. 9A, which corresponds to the embodiment illustrated in FIG. 1, a chip support inclines the surface of the chip with respect to the prism cover. In FIG. 9B, the sloped chip support is replaced with a sloped gasket that maintains the base of the prism cover in sloped arrangement with respect to the chip surface.

DETAILED DESCRIPTION OF THE INVENTION

Figure 1:
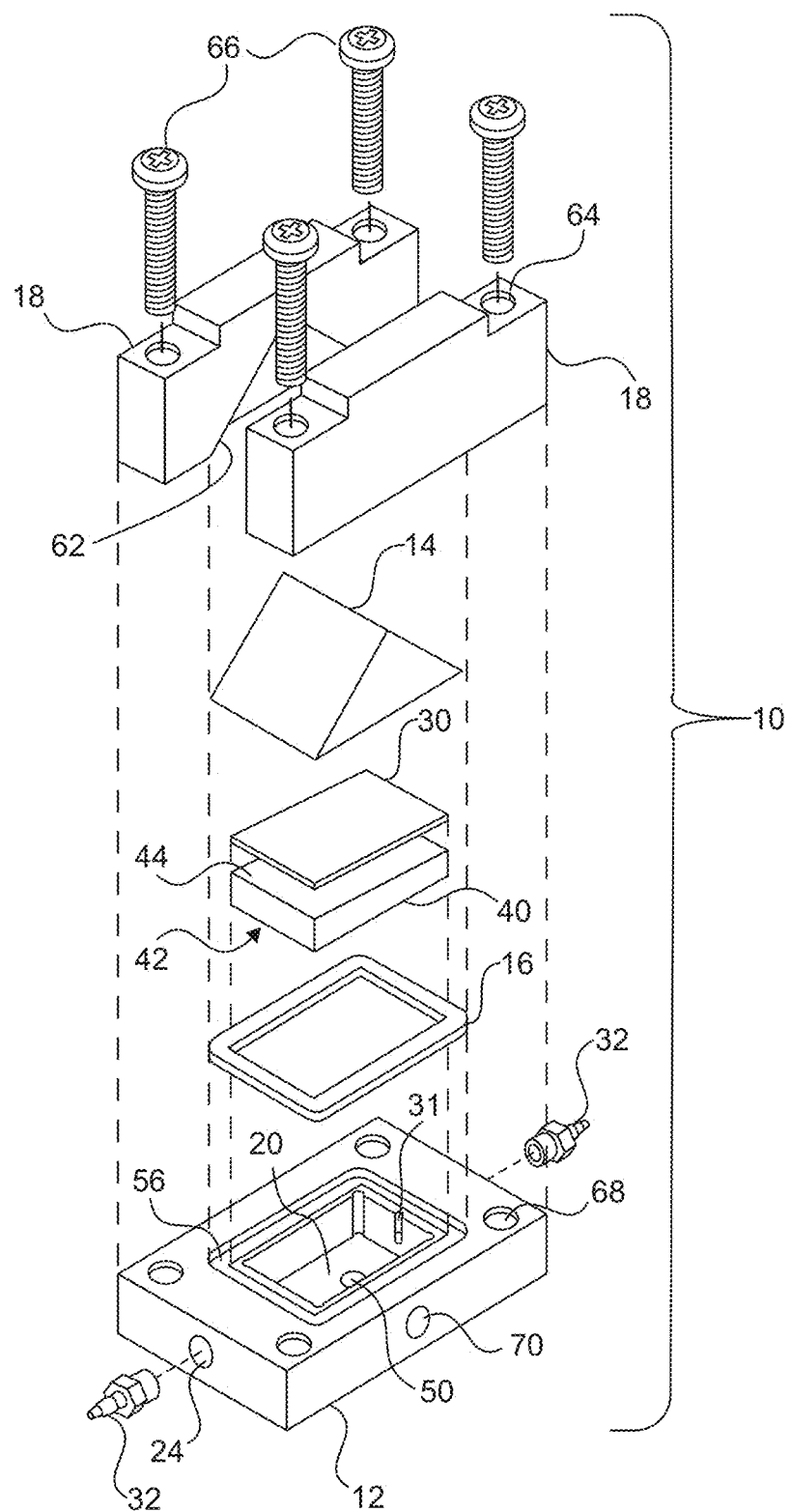
FIG. 1 is an exploded view of a flow cell according to a first embodiment of the present invention.
Figure 2:
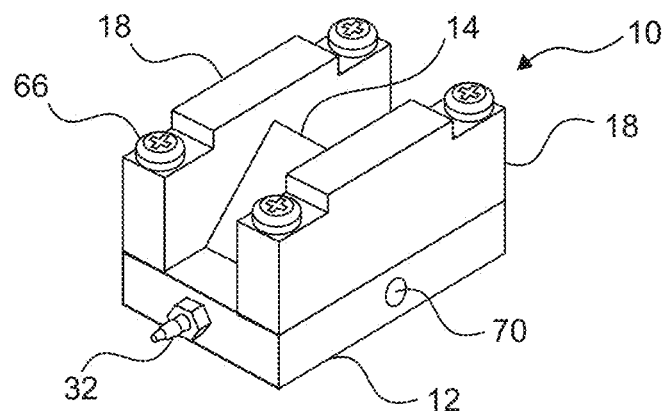
FIG. 2 is a perspective view of the flow cell illustrated in FIG. 1.
Figure 3:
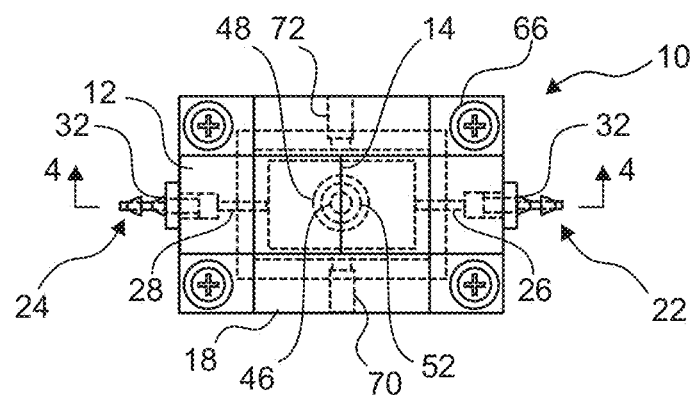
FIG. 3 is a top plan view of the flow cell illustrated in FIG. 1.
Figure 4:
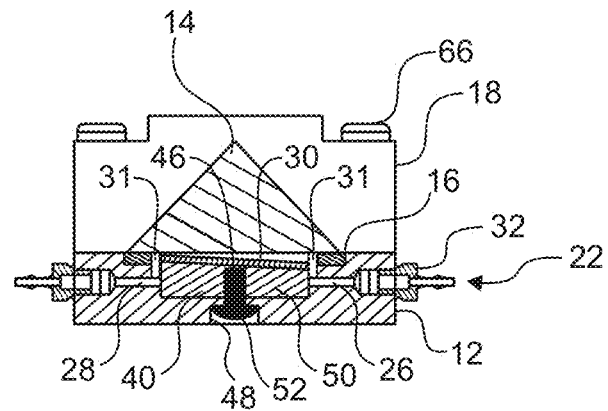
FIG. 4 is a cross-sectional view of the flow cell taken along line 4-4 in FIG. 3.

The present invention relates to detection systems and flow cells for use in carrying out arrayed imaging reflectometry-based detection of target molecules, typical biological or chemical molecules of interest. The fundamental basis of Arrayed Imaging Reflectometry ("AIR") is described in U.S. patent application Ser. No. 10/282,274 to Miller et al., filed Oct. 28, 2002, now U.S. Pat. No. 7,292,349, issued Nov. 6, 2007, which is hereby incorporated by reference in its entirety.

Basically, the detection system includes an appropriately structured chip that is capable of achieving a condition of near perfect (or complete) destructive interference when incident light is used to illuminate the chip surface at an appropriate angle of incidence. Thus, the detection system also includes a light source that is positioned to illuminate the chip and a detector that is positioned to detect light reflected from the surface of the chip. Depending upon the choice of light (e.g., wavelength), the materials that form the chip and the ambient environment (e.g., refractive indices involved), a particular angle of incidence can be selected such that the illuminating light produces a condition of near perfect destructive interference in the absence of the one or more target molecules and a substantial change (an increase) in light reflectivity in the presence of the one or more target molecules.

Briefly, the light source generates and transmits a light at a set wavelength towards a surface of the chip. Preferably, the light source is a tunable, collimated, monochromatic light source, although other types of light sources, such as a light source which is monochromatic, but not tunable or collimated could be used. Exemplary light sources include, without limitation, a light-emitting diode, a laser, or a lamp with a narrow bandpass filter. In addition, the light can be polarized in a single direction (i.e., either emitted from the light source as polarized light or passed through a polarizer). If an external polarizer is employed, it may be connected to a rotational driving system, such as a step motor, which can rotate the polarizer in the path of the light from the light source.

The light detector can be any suitable device capable of capturing light reflected from the chip surface, preferably an imaging array that captures an image of at least a substantial portion of the surface of the chip. Exemplary detectors include, without limitation, charge coupled device (CCD) sensor chips, complementary metal-oxide semiconductor (CMOS) sensor chips, or photodiode array detectors.

By condition of "near perfect destructive interference" or "near complete destructive interference", it is intended that the reflectivity of light (in the absence of bound target molecules) is less than about $10^{-4}$, more preferably less than about $10^{-5}$, most preferably less than about $10^{-6}$ or even less than about $10^{-7}$. The destructive interference of reflected light is caused by the simultaneous reflections from the medium/outer coating and outer coating/substrate or outer coating/intermediate coating interfaces. Upon binding of target molecules, reflectivity at the site of target binding can increase by up to several orders of magnitude. This affords devices with sensitivity to detect even femtomolar quantities of target molecules.

The basic set-up of the detection system also is disclosed in U.S. patent application Ser. No. 10/282,274 to Miller et al., filed Oct. 28, 2002, now U.S. Pat. No. 7,292,349, issued Nov. 6, 2007, which is hereby incorporated by reference in its entirety. Briefly, this includes a light source capable of producing polarized, preferably s-polarized light, a functionalized chip, and a detector that is positioned to capture reflected light from the chip surface.

The detection system of the present invention also includes a flow cell, described in greater detail below, and a fluid sample source (containing the fluid sample to be screened) in fluid communication with the inlet of the flow cell. The fluid sample is preferably an aqueous fluid, which is preferable for the detection of most biological targets. Exemplary target molecules that can identified include, without limitation, peptides, proteins, glycoproteins, peptidoglycans, carbohydrates, lipoproteins, a lipoteichoic acid, lipid A, phosphates, nucleic acids (DNA or RNA), whole pathogen (such as bacteria, virion, fungi, yeasts, protozoans, multicellular parasites, etc.), virus-like particles, whole cells, organic compounds (such as naturally occurring toxins or organic warfare agents, etc.), and combinations thereof. These target molecules can be detected from any source, including food samples, water samples, homogenized tissue from organisms, air, etc. If the sample to be tested is not initially in an aqueous medium, the sample can be diluted or dispersed in such as aqueous medium.

The flow cell includes first and second members that are secured together to define a substantially fluid-tight chamber that includes an inlet and an outlet (to allow flow of fluid across the surface of a chip designed for detecting target molecules). At least the second member is light transmissive. The chip includes a substrate, one or more reflective coating layers on the substrate, and one or more probe molecules tethered to the outermost coating layer. The chip is positioned inside the substantially fluid-tight chamber with the outermost coating layer and the one or more probe molecules thereon exposed to fluid in the chamber and facing the second member. Because the second member is light transmissive, illuminating light is allowed to pass through the second member where it is reflected from the chip surface. Depending on the presence of absence of target molecules bound to the probe surface, reflected light will be virtually undetectable in the absence of bound target (i.e., due to near perfect destructive interference) or detectable in the presence of bound target.

Exemplary light transmissive covers include both substantially flat and prismatic covers. Exemplary prismatic covers include, without limitation, triangular optic prisms (whether or not they are a 90° prism), and trapezoidal optic prisms. These covers can be formed of any suitable light transmissive materials, including glasses (e.g., oxide glasses and halide glasses), quartz, plastics, and polymeric materials. These light transmissive materials can be optically transparent or semi-transparent. The selection of glasses, quartz, plastics, and polymeric materials should be based on their refractive index.

Unlike chip structures optimal for detection in air, the chip structure for use in aqueous environments utilizes one or more suitably dimensioned coating layers formed over the substrate but which are appropriate for aqueous detection. Preferably, at least two layers are used so that the incidence angle of incident light can be optimized for use in the aqueous environment: an intermediate layer that forms an interface with the substrate, and an outermost coating layer that forms an interface with the intermediate layer as well as an interface with the aqueous medium. Additional intermediate layers can also be employed. It is the outermost coating layer to which probe molecules are attached.

There are a number of combinations of materials for the substrate and the one or more coating layers that are suitable for AIR in aqueous environments. These include, without limitation, the following substrate/intermediate coating/outer coating embodiments: $Si/SiN/SiO_2$, $Al_2O_3/Si/SiO_2$, $Si/SiN/Ta_2O_5$, or $Si/SiN/TiO_2$. In general, for any system selected, there are a number of thicknesses for each of the materials that will achieve optimal results when illuminated at an appropriate angle with light of a particular wavelength. The variable for each system includes the refractive indices of the materials, the material thicknesses, the angle of incidence for the illuminating light, and the wavelength of the illuminating light.

For example, using light at 632.8 nm with the $Si/SiN/SiO_2$ system having a SiN layer formed of silicon-rich non-stoichiometric silicon nitride with a thickness of ~85 nm and a $SiO_2$ layer thickness of ~203 nm, the optimal angle of incident light is about 38 degrees. This same system with the same light, but having a SiN layer thickness of ~100 nm and a $SiO_2$ layer thickness of ~237 nm, has an optimal angle of incident light that is about 64 degrees.

Also as an example when using light at 632.8 nm, for the $Si/SiN/TiO_2$ system having a silicon-rich non-stoichiometric SiN layer with thickness of ~25 nm and a $TiO_2$ layer thickness of ~62 nm, the optimal angle of incident light is about 47 degrees; whereas the same system having a SiN layer thickness of ~40 nm and a $TiO_2$ layer thickness of ~45 nm will have an optimal angle of incident light that is about 43 degrees.

With the $Si/SiN/Ta_2O_5$ system and light at 632.8 nm, a silicon-rich non-stoichiometric SiN layer having a thickness of ~25 nm and a $Ta_2O_5$ layer thickness of ~62 nm will have an optimal angle of incident light of about 47 degrees; whereas the same system having a SiN layer thickness of ~55 nm and a $Ta_2O_5$ layer thickness of ~25 nm will have an optimal angle of incident light of about 43 degrees, and a SiN layer thickness of ~85 nm and a $Ta_2O_5$ layer thickness of ~159 nm will have an optimal angle of incident light of about 41 degrees.

Thus, the variability of incidence angles—even for monochromatic light—is relative to the thickness of the intermediate and outer coating layers and their refractive indices. Additional variations can be achieved with different wavelengths of light.

The binding chemistry for coupling of probes to the outermost layer is described in U.S. patent application Ser. No. 10/282,274 to Miller et al., filed Oct. 28, 2002, now U.S. Pat. No. 7,292,349, issued Nov. 6, 2007, which is hereby incorporated by reference in its entirety, and therefore is not repeated here. Exemplary probes include, without limitation, non-polymeric small molecules, peptidomimetic compounds, polypeptides or proteins, oligonucleotides, and combinations thereof. Other types of probe molecules, including polymers, can also be employed.

Preferably, the one or more probe molecules are present in the form of a plurality of distinct probes tethered to distinct locations or spots on the outermost coating layer in an array. In this embodiment, it is possible to construct arrayed imaging chips capable of detecting a substantial number of targets (e.g., greater than $10^5$ or $10^6$) in one or more fluid samples being examined. In the arrayed imaging chips, each of the distinct locations or spots contains substantially a single type of probe molecule. It is also possible to construct the chip so that each distinct location or spot contains two or more types of probe molecules.

Referring to FIGS. 1-4, a flow cell 10 in accordance with one embodiment is illustrated. The flow cell 10 includes a base (or first member) 12, a light transmissive cover (second member) 14 in the form of a 90° prism, a gasket 16 positioned between the base and cover, and one or mounting braces 18 that are utilized to secure the base and cover in a substantially fluid-tight manner.

The base 12 includes a well 20 formed in one face thereof, as well as inlet 22 and outlet 24 that communicate with the well via passages 26 and 28, respectively. Inlet 22 and outlet 24 are formed on opposite ends of the base such that the passages 26 and 28 that communicate with the well 20 ensure fluid flow over chip 30 when it is placed in the well. To assist with fluid flow in this respect, a notch 31 is formed in the sidewall of well 20 at each end of the well such that fluid can easily flow into the well from passage 26 and from the well via passage 28. The passages 26 and 28 are preferably provided with fittings 32 that allow conduits or other forms of tubing to be coupled to the flow cell. For example, the fluid sample source can be coupled to the inlet 22 and the outlet 24 can be coupled to additional fluid analyzers or simply to a waste reservoir.

The chip 30 is preferably supported in the well 20 by an angled chip support 40. The chip support 40 has a substantially planar first surface 42 designed to rest against the bottom of well 20, and a sloped planar surface 44 designed to support chip 30. The slope of the surface 44, relative to surface 42 and a face of the cover 14, can be about 1° up to about 5°, more preferably about 1° up to about 3°, most preferably about 2°. The support 40 also includes a threaded bore 46.

In the opposite face of the base 12 in which the well 20 is formed, a shouldered recess 48 and bore 50 are provided. A threaded machine screw 52 (or other appropriate connecter) passes through bore 50 to engage the threaded bore 46 of the chip support 40. This allows the chip support 40 to be tightly retained against the bottom of the well 20 in a substantially fluid-tight manner. A gasket may optionally be used between the bottom of the well 20 and the chip support 40 as needed.

In the surface of the base 12 in which well 20 is formed, a shallow recess 56 is provided about the perimeter of the well. The shallow recess 56 is designed to receive gasket 16, and thereby seal the well during use when the base 12 and cover 14 are secured together.

As shown, the base 12 and cover 14 are secured together by a pair of mounting braces 18. Each mounting brace includes an appropriately contoured surface 62 that is designed to engage or receive the cover, and two bores 64 through which machine screws 66 are used to secure the mounting braces to the base 12. The base 12 is provided with a number of threaded receptacles 68 designed to receiving machine screws 66. It should be appreciated that in some embodiments the two mounting braces could be fused together to form a single mounting brace designed to engage the cover. Any number of machine screws or other suitable fasteners can be used so as to ensure a substantially fluid-tight well.

The use of mounting braces and removable machine screws allows for replacement of the chip 30 and re-use of the flow cell. It should be appreciated, however, that the flow cell could also be fabricated with the base and cover permanently secured or fused together via any appropriate means, e.g., sonic welding, adhesives, etc. These constructions would be intended for limited re-use.

In the opposed sides walls of the base 12 are a pair of opposed threaded recesses 70, 72. Each of recesses 70, 72 is adapted to receive a set screw for mounting of the device onto a goniometer or rotation stage, which allows for precision tuning of the incident angle.

Figure 5:
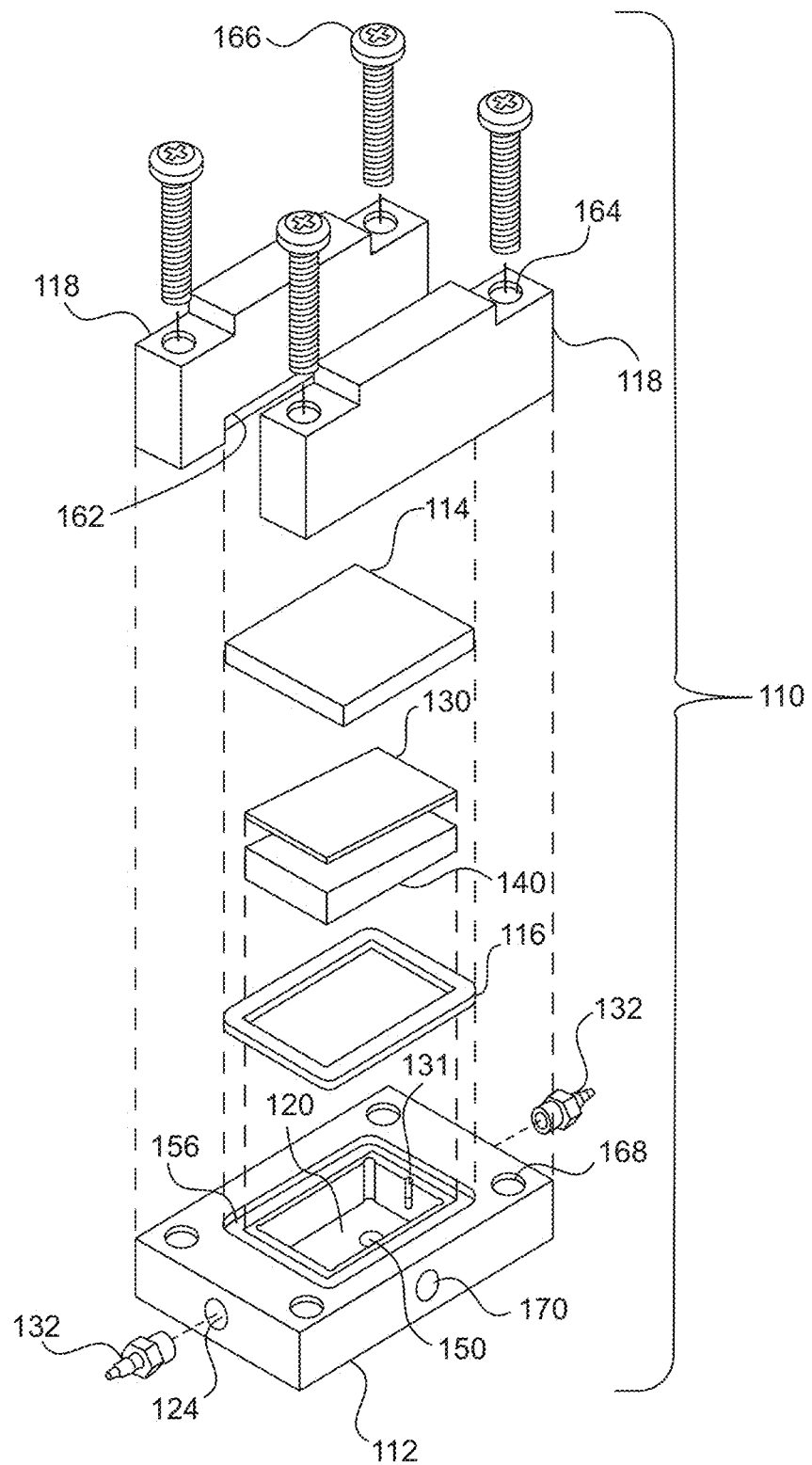
FIG. 5 is an exploded view of a flow cell according to a second embodiment of the present invention.
Figure 6:
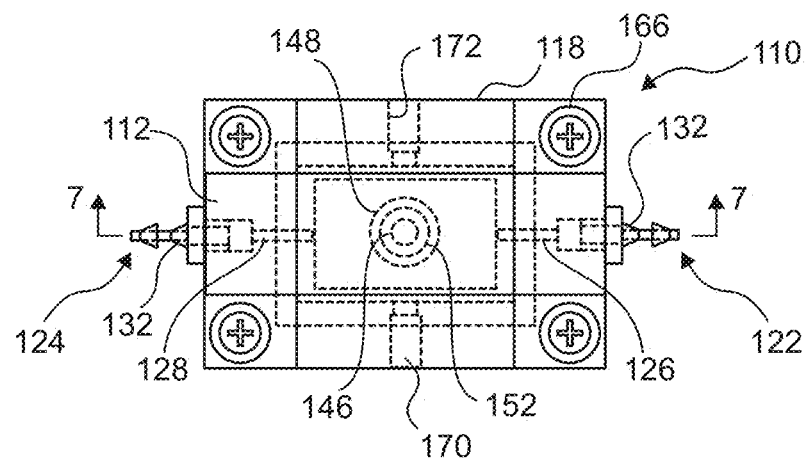
FIG. 6 is a top plan view of the flow cell illustrated in FIG. 5.
Figure 7:
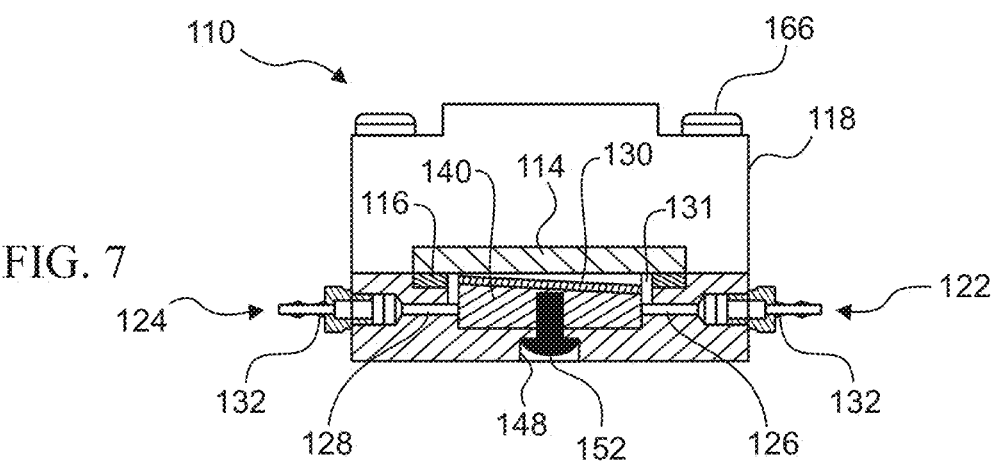
FIG. 7 is a cross-sectional view of the flow cell taken along line 7-7 in FIG. 6.

Referring to FIGS. 5-7, a flow cell 110 in accordance with a second embodiment is illustrated. The flow cell 110 includes a base (or first member) 112, a light transmissive cover (second member) 114 in the form of a substantially flat covering material such as $SiO_2$ glass, a gasket 116 positioned between the base and cover, and one or more mounting braces 118 that are utilized to secure the base and cover in a substantially fluid-tight manner. The construction of the flow cell 110 is largely identical to the embodiment illustrated and described above with respect to flow cell 10 (FIGS. 1-4) except that the cover 114 and mounting braces 118 have been modified. Specifically, the countered surfaces 162 of mounting braces 118 have been adapted to the different configuration of cover 114. The mounting braces 118 are coupled to base member 112 in the same manner as described for the embodiment illustrated in FIGS. 1-4 (i.e., machine screws 166).

During use of the flow cell, the chip support 40, 140 and chip 30, 130 will be placed into the well 20, 120 and secured in place with machine screw 52, 152 (which pass through bores 50, 150 in the base 12, 112). Thereafter, the gasket 16, 116 and cover 14, 114 will be positioned over the well 20, 120 and secured via mounting braces 18, 118 and machine screws 66, 166. Upon connection of the inlet 22, 122 and outlet 24, 124 fittings 32, 132 to tubing or other conduit that is in communication with a fluid sample source and downstream fluid handling (waste or further analysis), fluid can be introduced into the well 20, 120 of the flow cell and detection of any target in the sample can commence. Basically, detection is carried out by directing light at the one or more coatings on the chip in a manner effective to result in a condition of near perfect destructive interference (in the absence of any target) and measuring light reflected from the chip. Upon binding of target molecules to the one or more probes tethered to the outermost coating on the chip, a change in the refractive index occurs and a loss of interference is detected by a measurable increase in the light reflected from the chip. The measurement of light by the detector can produce an image or other form of output that identifies the presence of at least one target based on the measurement of reflected light (i.e., the loss of interference).

Figure 8:
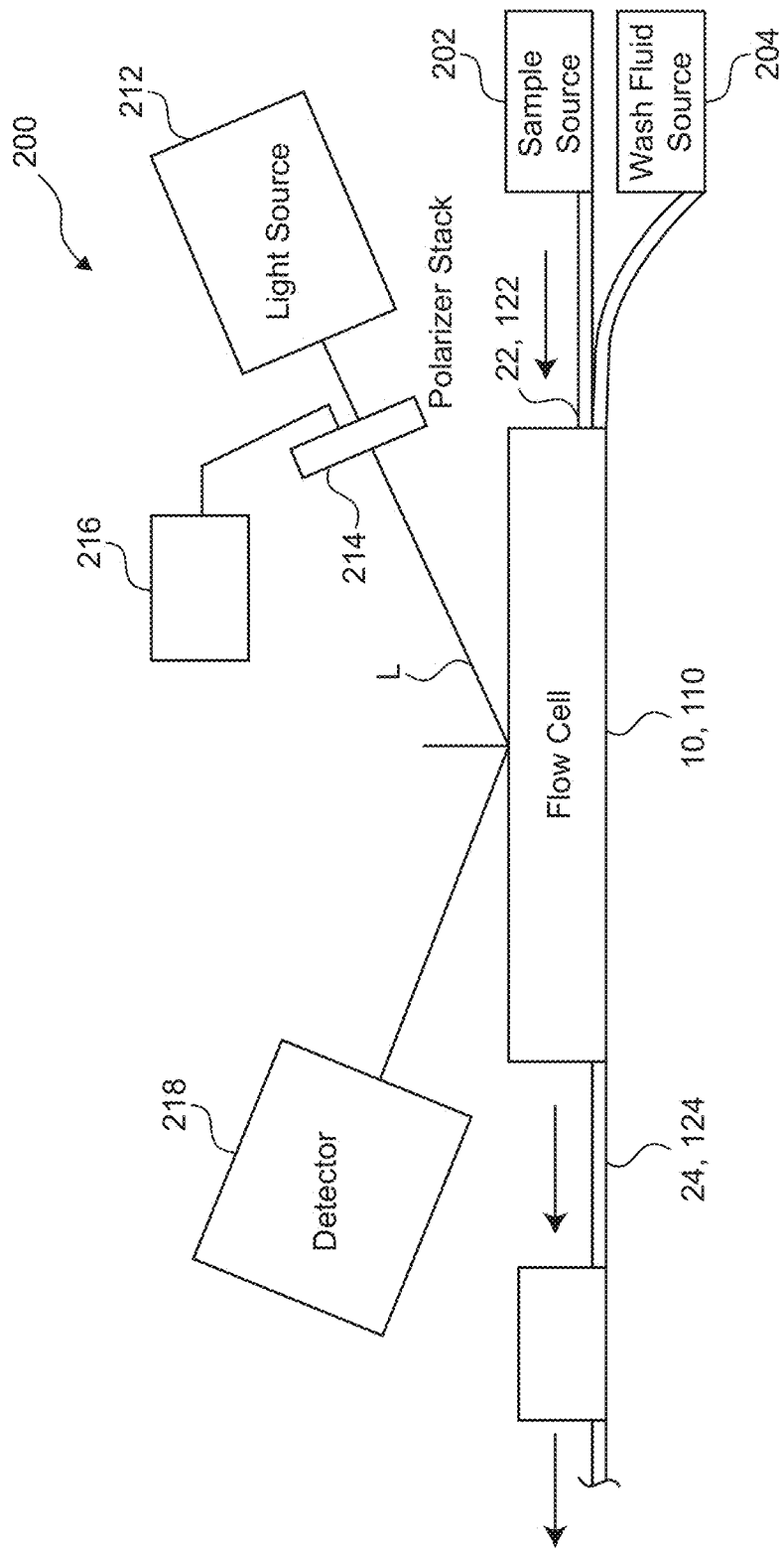
FIG. 8 illustrates an AIR detection system that includes a flow cell of the present invention. Although a flow cell according to the first embodiment (FIGS. 1-4) is illustrated, the detection system is not limited to this embodiment.

As illustrated in FIG. 8, a detection system 200 suitable for AIR is illustrated. The flow cell 10, 110 is shown coupled to a sample source 202 and a wash fluid source 204 at inlet 22, 122. The sample source 202 includes an aqueous solution comprising a sample that is intended to flow through the flow cell. The wash fluid source 202 preferably contains an aqueous buffer solution, but may include buffer solutions that create higher stringency conditions for removal of any target molecules that are non-specifically bound to the chip surface. It is contemplated that the detection system may optionally contain more than one sample source 202 and/or more than one wash fluid source 204. Where more than one sample source 202 is present, each sample source can contain a different sample or each can contain replicates of the same sample. Where more than once sample source contains different samples, it is also possible to utilize the system to detect multiple layers of biomolecular interactions, termed "cascade sensing." Thus, a target molecule, once bound, effectively becomes a probe for a secondary target molecule. This can involve detection of small molecule recognition events that take place relatively far from the chip surface.

It is also contemplated that the detection system 200 can be used with an automated delivery system for delivery of the samples from the sample source(s) 202 and the wash solution from the wash fluid source(s) 204.

Figure 9A:
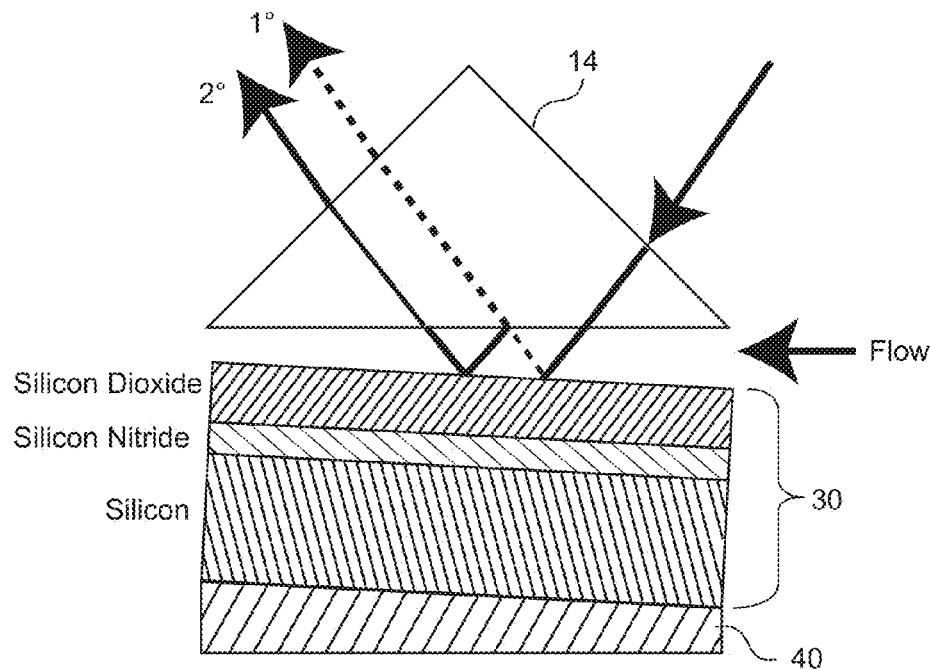
FIGS. 9A-B are schematic images of two versions of the flow cell, which depict incident light coupled into and out of the substrate system. The primary signal (1°) carries the interference pattern, whereas the secondary (reflected) signal (2°) is disregarded.
Figure 9B:
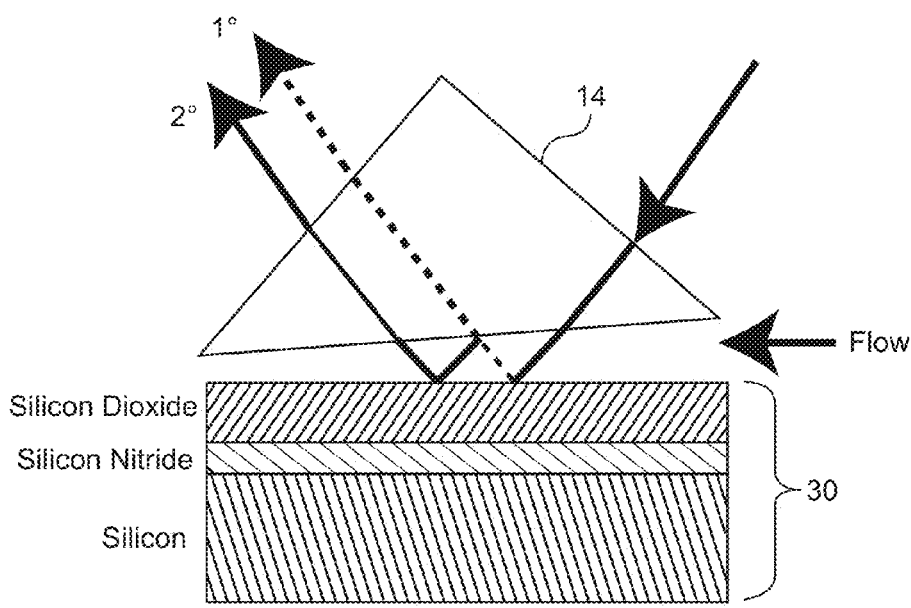

The detection system 200 includes, a light source 212, a polarizer 214 with optional step motor 216, a flow cell 10, 110, and a detector 218. The light source 212 generates and transmits a light (L) at a set wavelength towards the second member 14, 114, which couples light into the flow cell at an appropriate incident angle to the exposed surface of the chip present within the well of the flow cell. FIG. 9A is an enlarged schematic view that illustrates the role of the prism-based flow cell 10 in coupling incident light onto the chip. The chip is inclined or biased toward the incident light using a sloped chip support. Two distinct beams of light are labeled as exiting the prism, and they are generally denoted the primary (1°) and secondary (2°) reflectances. The primary reflectance (1°) contains all of the information for the system; the secondary reflectance (2°) contains no usable information and is preferably blocked by downfield optics. As an alternative to using the chip support shown in FIG. 9A, the gasket material on which the cover rests can be tapered along the length of the device, i.e., thicker at one end and thinner at the other end, such that the cover (in this case, the prismatic cover) has its base inclined with respect to the chip surface. This inclination of the cover, shown in FIG. 9B, achieves substantially the same effect as inclination of the chip relative to the cover (i.e., a slope of 1° to about 5° or as otherwise noted above).

Downfield blocking of the secondary reflectance has been achieved using a beam stop, such as a solid piece of metal, as well as an iris (positioned just past the imaging lens) that blocks out the secondary reflection while allowing the primary reflection to pass. As an alternative, the detector (as its imaging optics) can be positioned off the axis of the secondary reflection such that no secondary reflection can be detected. Referring again to FIG. 8, it is the primary reflectance whose output is detected by detector 218.

The image capture can be achieved by any of the detectors described above, but preferably via an image array detector that captures an image of at least a substantial portion of the surface of the chip. For arrays of hundreds to hundreds of thousands of probes, an automated chip reader can be programmed to assess the change in reflectivity for each spot on an array based on the captured image.

Also illustrated in FIG. 8 is a downstream analyzer 230, which can analyze the fluid(s) that pass from the outlet 24, 124 of the flow cell. Thus, these fluid(s) can also be recovered and/or analyzed separately from the AIR approach described above. Further analysis can include, without limitation, ELISA, PCR, realtime-PCR, mass spectrometry, and liquid chromatography-NMR spectroscopy. Moreover, after detecting the presence of a target during use of the chip, the target itself can be dissociated from the one or more probes to which it was bound during use of the device. Dissociation can be achieved by any of a variety of ways, where the means for dissociation depend largely on the nature of probe-target coupling. Exemplary approaches include, without limitation, a glycine solution at low pH, a low pH water solution, a high pH water solution, a concentrated salt solution, a detergent solution (with low, moderate, or high concentrations), a low concentration denaturant solution (e.g., urea). After dissociation, the target molecule (now free from the chip surface) can be recovered and then analyzed (e.g., by mass spectrometry, NMR-spectroscopy, optical fluorescence absorbance spectroscopy, etc.). Depending on the approach of subsequent down-stream analysis, it is possible to use the eluted samples directly or following one or more steps for concentration of the analyte(s) of interest. The above-noted techniques allow for the study of solution-phase interactions as well as the elucidation of mass/structural information.

EXAMPLES

The present invention may be further illustrated by reference to the following examples.

Example 1

Manufacture of Chip Having Si-substrate/SiN/SiO$_2$ Coatings for Arrayed Imaging Reflectometry To design an appropriate substrate for underwater s-polarized AIR, using a flow cell of the type described herein, simulations were conducted on several materials systems. The overall goal was to maintain the high sensitivity of the "dry" AIR system (Si/SiO$_2$), while allowing for a physically reasonable incident angle of light coupling into the flow cell apparatus. While Si/SiN system possesses the appropriate optical properties, this system was deemed undesirable for initial testing because of the difficulty of achieving covalent attachment of probe molecules to the nitride coating and minimal control over the layer thickness.

The difficulty with Si/SiN was overcome by using an Si/SiN/SiO$_2$ system. Silicon dioxide is readily functionalized with biomolecular probes (see U.S. patent application Ser. No. 10/282,274 to Miller et al., filed Oct. 28, 2002, now U.S. Pat. No. 7,292,349, issued Nov. 6, 2007, which is hereby incorporated by reference in its entirety). Moreover, its thickness can be finely tuned with hydrofluoric acid etching. Due to this control over the SiO$_2$ layer thickness, any inaccuracies in the initial SiN layer thickness can be accommodated by varying the SiO$_2$ layer thickness.

Coating of a previously etched (to remove native oxide layer) silicon substrate was achieved by low stress (<200 MPa), low pressure chemical vapor deposited (LPCVD) silicon nitride by MEMS-exchange. This SiN coating is a non-stoichiometric, silicon-rich SiN coating. Silicon dioxide was then sputter deposited onto the Si/SiN wafer to a thickness greater than the desired final coating. This facilitated fine-tuning of the coating thickness via etching. The resulting chip contained a ~88 nm thick SiN layer, coated by a 200.7 nm thick SiO$_2$ layer. This produces optimal results for an HeNe light source (632.8 nm) and a 44.080 incident angle.

Example 2

Design and Modeling of Flow Cell Containing Chip Having Si Substrate/SiN/SiO$_2$ Coatings FIG. 9A is an image simplifying the role of the prism-based flow cell (according to FIGS. 1-4) in coupling incident light onto the chip. Two distinct beams of light are labeled as exiting the prism, and they are generally denoted the primary (1°) and secondary (2°) reflectances. The primary reflectance (1°) contains all of the information for the system; the secondary reflectance (2°) contains no usable information and is preferably blocked by downfield optics. To separate these two distinct reflections, the substrate of the chip is placed on the angled chip support inside the flow cell.

Figure 10:
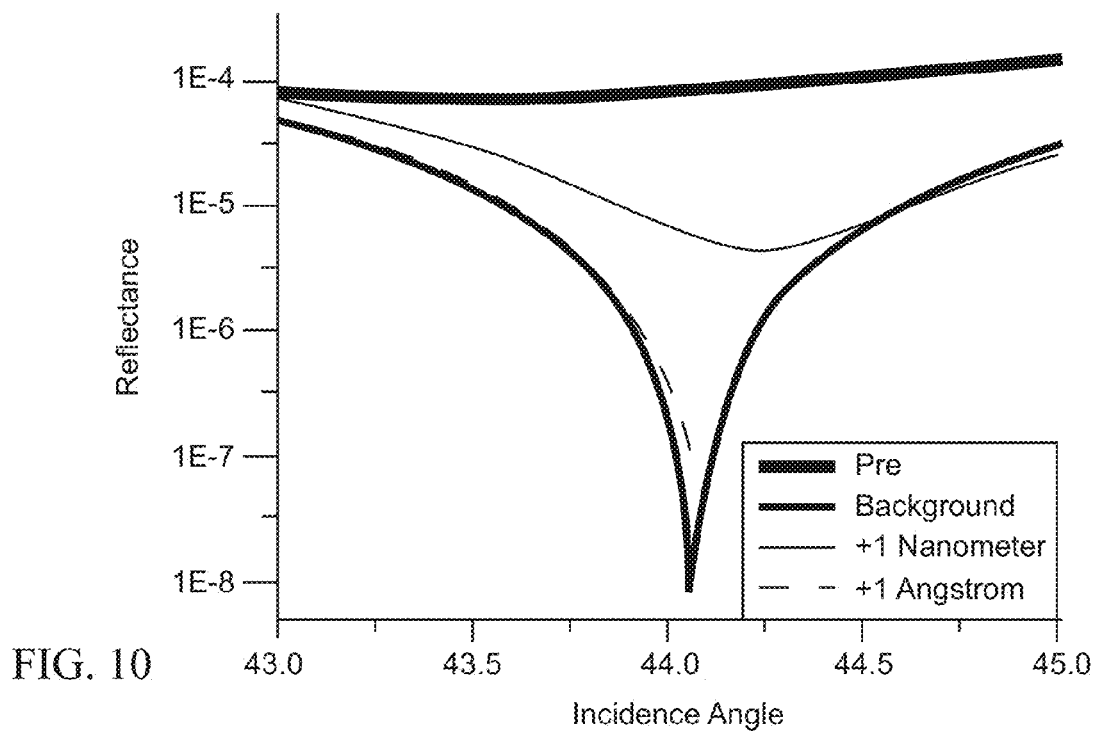
FIG. 10 is a graph illustrating simulated reflectance spectra of the substrate system illustrated in the first embodiment. The probe-functionalized chip surface is capable of achieving a condition of near perfect destructive interference having a reflectance of about $10^{-7}$ or less. Binding of a target molecule that achieves ~1 nm change in thickness to the chip produces a significant change in reflectance ($10^{-4}$ minima) to the extent of about three orders of magnitude. Binding of a target molecule that achieves ~1 Å change in thickness to the chip produces a significant change in reflectance ($10^{-5}$ minima) to the extent of about two orders of magnitude.

FIG. 10 is an overlay of the reflectance spectra obtained from simulating the propagation of light within the Si-substrate/SiN/SiO$_2$ system. "Pre" represents the bare chip (Si-substrate/SiN/SiO$_2$) without any probe molecules coupled to the SiO$_2$ coating; and "Background" represents the coupling of probe molecules onto the SiO$_2$ coating. With the coupling of the probe molecules, the system achieves near perfect destructive interference with less than ~$10^{-8}$ reflectance. Upon binding of 1 Å of target material, the reflectance spectrum shifts upward by nearly one order of magnitude (~$10^{-7}$ reflectance). But upon binding 1 nm of target material, the reflectance shifts upward by well over two orders of magnitude (~$5 \times 10^{-5}$).

Because AIR is not a spectral technique, only pure changes in reflectance are observed. In the modeling shown in FIG. 10, this corresponds to ΔR/R values of approximately 41,500% and 560% for binding one nanometer and one Angstrom, respectively. Even for binding ~1 picometer of material, the ΔR/R is still a measurable 1.6%. In other words, target molecules that cause sub-Angstrom level changes in thickness are sufficient for detection using a system of this present invention.

Example 3

Arrayed Imaging Reflectometry Using Si Substrate/SiN/SiO$_2$ Chip to Demonstrate Change in Reflectance During Underwater-Detection of Bovine Serum Albumin Using a chip having a structure described above (Si-substrate/SiN/SiO$_2$), bovine serum albumin was spotted onto the surface of the chip without use of a probe. The chip was submerged under water, and then the reflectivity of the chip was detected using a system of the type described above and illustrated in U.S. patent application Ser. No. 10/282,274 to Miller et al., filed Oct. 28, 2002, now U.S. Pat. No. 7,292,349, issued Nov. 6, 2007, which is hereby incorporated by reference in its entirety).

Figure 11A:
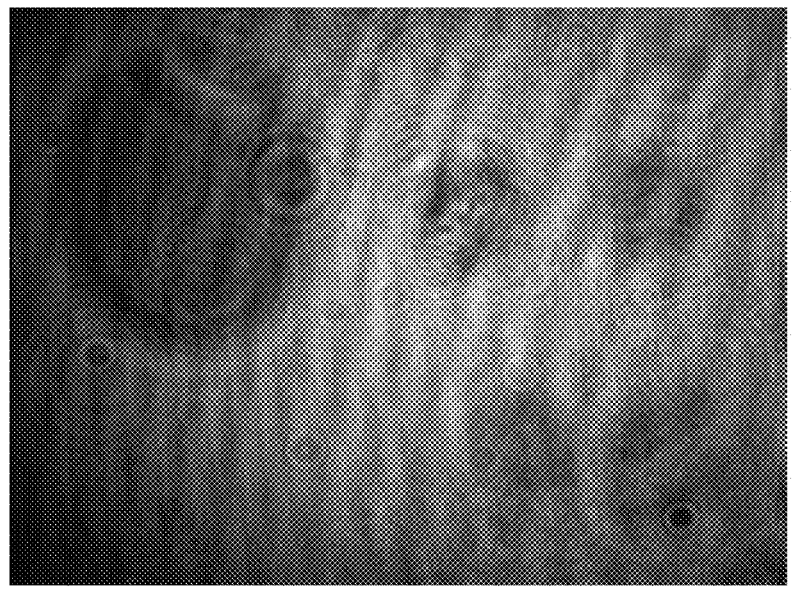
FIGS. 11A-B are images of an array of adsorbed bovine serum albumin ("BSA") on the surface of a Si-substrate/SiN/SiO$_2$ chip under water. BSA spots are outlined in FIG. 11B, but are clearly visible without outlining in FIG. 11A.
Figure 11B:
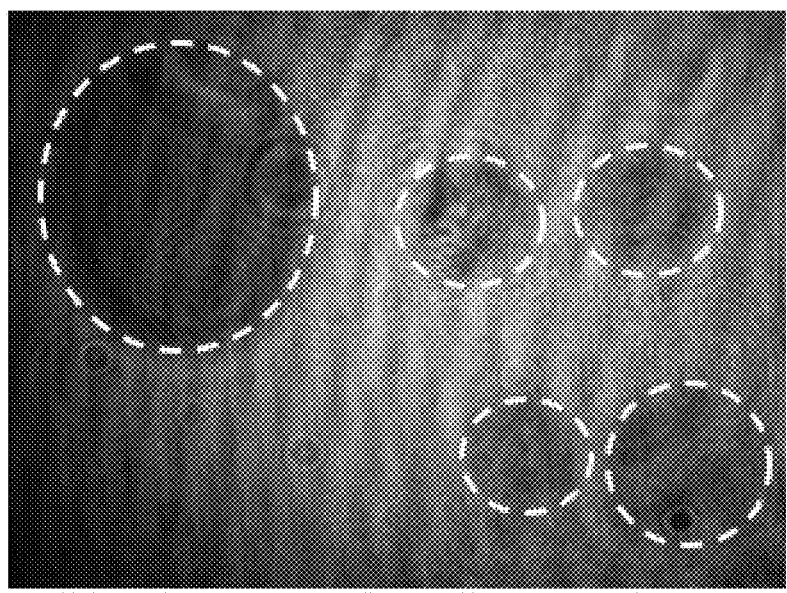

The resulting image obtained from the detector is shown in FIG. 11A. The BSA spots are visible to the naked eye, as evidenced by the enhanced image in FIG. 11B where the BSA spots are circled.

Example 4

Figure 12:
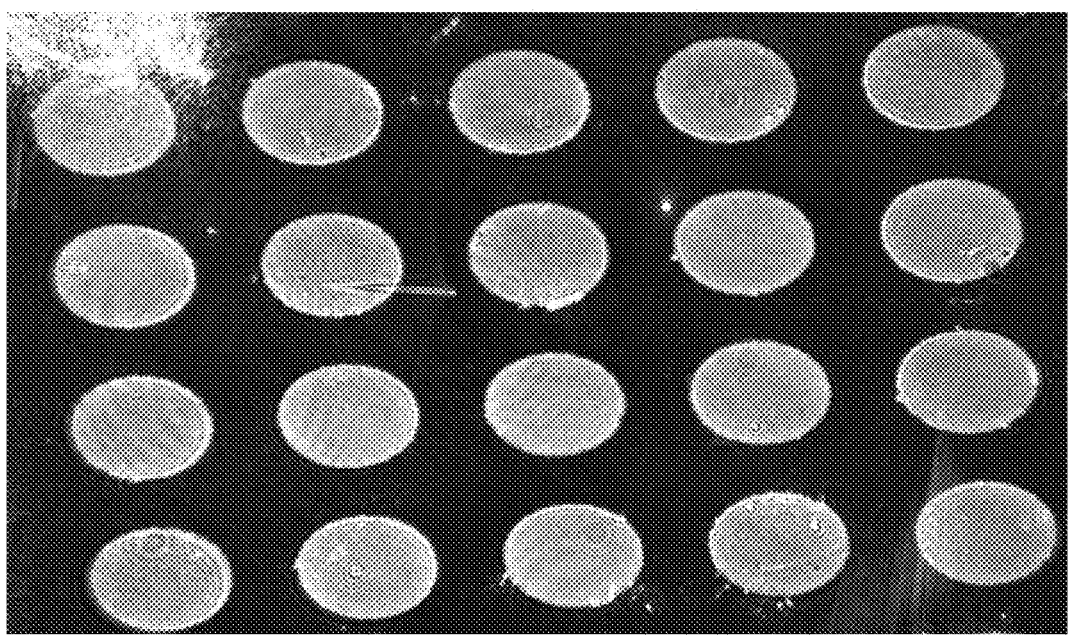
FIG. 12 is an image of an array of 65 Å steps of silicon dioxide on the base aqueous arrayed imaging reflectometry chip—Si-substrate/SiN/SiO$_2$ as described above—that was patterned by photolithography of the top SiO$_2$ layer.

Arrayed Imaging Reflectometry Using Si Substrate/SiN/SiO$_2$ Chip to Demonstrate Change in Reflectance FIG. 12 is an image of an array of 65 Å steps of silicon dioxide on the base aqueous arrayed imaging reflectometry substrate—Si/SiN/SiO$_2$ structure described above—that was patterned by photolithography and hydrofluoric acid etching of the top SiO$_2$ layer. Each spot is circular and 500 µm in diameter, although they appear slightly elliptical due to the ~45° angle of incidence that is used to achieve the near total destructive interference of light reflected off of the aforementioned substrate. The image was acquired with the chip mounted on a 3° wedge while the flow cell apparatus was under flow with an aqueous phosphate buffer as controlled by a syringe pump.

To exactly position the flow cell at the optimal angle of incidence, the entire apparatus (by means of an attached goniometer) was successively rotated about either side of the presumed minimum in order to map the angular dependence of the observed reflectance intensity/contrast and tune the angle of incidence to map out the reflectance minimum to 44.08°. After positioning the flow cell at the proper angle of incidence to achieve near total destructive interference, the image of FIG. 12 was acquired.

This example demonstrates that chip features can be observed on the designed substrate in a controlled manner. This patterned chip was subsequently used to optimize wedge angle to about 2° to about 3°. The lower angle was shown to be optimal to reduce flow cell volume, while the larger angle was optimal for separating the primary and secondary reflectances. Thus, any angle in between about 2° to about 3° can produce optimal results. This patterned chip was also used to establish the stability of the observed reflectance as a function of time, and characterize the intensity as a function of the spatial location relative to the chip center.

Example 5

Functionalization of Si Substrate/SiN/SiO$_2$ Chip with Protein Probe Molecule

This example describes the covalent attachment of any protein via its primary amines. The following steps are taken to prepare the chip surface:
1) The outer coating (SiO$_2$) of the AIR chip will be finely tuned to the experiment's target thickness using a series of dilute hydrofluoric acid etches.
2) The chip will be washed for 30 minutes in a 1:1 solution of hydrochloric acid to methanol.
3) The chip will be thoroughly washed with double distilled water (ddH$_2$O).
4) The chip will then be submersed for 15 minutes in a solution of aminopropyl triethoxysilane (APTES): 0.25% APTES in 95% acetone and 4.75% ddH$_2$O.
5) The chip will be thoroughly washed with ddH$_2$O and then dried with a stream of nitrogen (N$_2$).
6) The chip will then be cured at 100° C. for 15 minutes.

At this point the chip surface will be functionalized with a terminal amine. A variety of hetero- and homo-bifunctional crosslinking chemicals may now be used to facilitate covalent attachment of protein probe molecules to the chip surface. These crosslinkers include, but are not limited to, glutaraldehyde, p-phenylene diisothiocyanate, disuccinimidyl carbonate, and N-succinimidyl 4-maleimidobutyrate. These following steps below will focus on the use of glutaraldehyde.
7) The chip will be immersed for about 60 minutes in a solution of 1.25% glutaraldehyde in phosphate buffered saline.
8) The chip will then be thoroughly washed with ddH$_2$O and then with acetone, and the chip will be dried with a stream of N$_2$.

At this point the chip surface will be functionalized with a terminal aldehyde. The user may choose to reduce the resulting reversible imine linker (APTES pendant amine to the alpha-aldehyde of glutaraldehyde) to an irreversible secondary amine. Regardless, the surface will then be functionalized with a terminal aldehyde for the covalent attachment of a probe protein or polypeptide via any accessible amine.
9) The probe protein(s) (e.g., streptavidin, antibody, or any other protein or polypeptide with specificity to its target molecule) will be diluted in an appropriate buffer and introduced to the chip surface, either by manual or robotic means, and allowed to immobilize for about 60 minutes.
10) The chip will be washed with ddH$_2$O.
The chip is now properly prepared and receptive for specific and selective detection of target molecules. The chip can be installed into the flow cell of the invention, which is present in a detection system of the type illustrated in FIG. 8.

Example 6

Functionalization of SiO$_2$/SiN/Si Chip with DNA Probe

DNA oligonucleotide probe strands can also be attached to the Si substrate/SiN/SiO$_2$ chip surface using similar methods to those described in Example 5. For example, purchased DNA oligonucleotides are frequently modified with primary amines. As such, these DNA oligonucleotides can be covalently attached to the chip using the protocol outlined above.

Alternatively, another common modification to purchased DNA oligonucleotides probe strands is a pendant biotin moiety. To immobilize these probe molecules, a lawn of streptavidin or avidin must first be covalently attached to the chip. This may be done through the steps outlined in Example 5 above, where the protein in step 9 is streptavidin or avidin. After washing and drying the chip (see step 10), the following steps can be followed:
11) The probe oligonucleotide strand(s) will be diluted in an appropriate buffer and introduced to the chip surface, either by manual or robotic means, and allowed to immobilize for about 60 minutes.
12) The chip will then be washed with ddH$_2$O.
13) The remaining biotin binding sites of the streptavidin/avidin lawn will be quenched with an excess solution of biotin for about 15 minutes.

After washing, this chip is now properly prepared and receptive for specific and selective detection of target molecules that will bind to the oligonucleotide probe under appropriate conditions. The chip can be installed into the flow cell of the invention, which is present in a detection system of the type illustrated in FIG. 8. Target molecules that can be detected with this type of chip include, without limitation, nucleic acid molecules that bind via Watson-Crick base pairing (e.g., DNA and RNA), as well as nucleic acid molecules or proteins that selectively bind via non Watson-Crick base-pairing.

It should be appreciated by those of skill in the art, that similar approaches can be used to immobilize RNA probe molecules. Such RNA probe molecules can also bind to these same types of target molecules via Watson-Crick base pairing or via non Watson-Crick base-pairing.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A flow cell for use in an arrayed imaging reflectometry detection system, the flow cell comprising:
    first and second members that are secured together to define a substantially fluid-tight chamber having an inlet and an outlet, at least the second member being light transmissive; and
    a chip comprising a substrate, one or more coating layers on the substrate, and one or more probe molecules tethered to the outermost coating layer, the one or more coating layers are suitably dimensioned to create a condition of near perfect destructive interference upon exposure to s-polarized light of a suitable wavelength at a specific incidence angle, and in the absence of the one or more target molecules binding to the one or more probe molecules, the chip being positioned with the outermost coating layer and the one or more probe molecules thereon exposed to aqueous fluid in the chamber and facing the second member, whereby a substantial change in s-polarized light reflectivity from the chip occurs in the presence of the one or more target molecules.

2. The flow cell according to claim 1, wherein the second member is a prism.

3. The flow cell according to claim 1, wherein the second member is substantially flat.

4. The flow cell according to claim 1, wherein the second member comprises a glass, quartz, plastic, or polymer that is optically transparent or semi-transparent.

5. The flow cell according to claim 1 further comprising a gasket positioned between the first and second members.

6. The flow cell according to claim 5 wherein the gasket has a tapered thickness from one end of the flow cell to the other end of the flow cell, thereby maintaining the surface of the second member at an angularly sloped position relative to the chip.

7. The flow cell according to claim 6 wherein the gasket is sloped at an angle of about 1° to about 5°.

8. The flow cell according to claim 1 further comprising one or more mounting braces that secure the first and second members together.

9. The flow cell according to claim 1 further comprising an angled support positioned within the chamber, wherein the chip is adjacent to the angled support.

10. The flow cell according to claim 9 wherein the angled support comprises a face, against which the chip rests, that is sloped at an angle of about 1° to about 5° relative to a face of the second member.

11. The flow cell according to claim 1 wherein the one or more coating layers comprise two or more coating layers.

12. The flow cell according to claim 11 wherein the substrate and the two or more coating layers comprise Si substrate/SiN/SiO$_2$, Si substrate/SiN/Ta$_2$O$_5$, Si substrate/SiN/TiO$_2$, or Al$_2$O$_3$ substrate/Si/SiO$_2$.

13. The flow cell according to claim 1 wherein the one or more probe molecules comprise a plurality of distinct probe molecules tethered to distinct locations on the outermost coating layer in an array.

14. The flow cell according to claim 13 wherein each of the distinct locations comprises substantially a single type of probe molecule.

15. The flow cell according to claim 13 wherein each of the distinct locations comprises two or more types of probe molecules.

16. A detection system comprising:
    a flow cell comprising:
        first and second members that are secured together to define a substantially fluid-tight chamber having an inlet and an outlet, at least the second member being light transmissive; and
        a chip comprising a substrate, one or more coating layers on the substrate, and one or more probe molecules tethered to the outermost coating layer, the chip being positioned with the outermost coating layer and the one or more probe molecules thereon exposed to aqueous fluid in the chamber and facing the second member, whereby light passing through the second member and the aqueous fluid is reflected by the chip; and
        wherein the one or more probe molecules specifically bind to one or more target molecules;
    an aqueous sample source in fluid communication with the inlet of the flow cell;
    a light source that is positioned to illuminate the chip with s-polarized light; and
    a detector that is positioned to detect light reflected from the surface of the chip, wherein the one or more coating layers are suitably dimensioned and the angle of incidence of the illuminating s-polarized light is suitable to produce a condition of near perfect destructive interference in the absence of the one or more target molecules and a substantial change in s-polarized light reflectivity in the presence of the one or more target molecules.

17. The detection system according to claim 16 wherein (i) the light source emits s-polarized light or (ii) the system further comprises at least one s-polarizer positioned between the light source and the chip and in a path of light emitted from the light source.

18. The detection system according to claim 16 wherein the light source directs the light toward the coating at a non-normal angle of incidence.

19. The detection system according to claim 16 wherein the substrate and the one or more coating layers are selected from the group of Si substrate/SiN/SiO$_2$, Al$_2$O$_3$ substrate/Si/SiO$_2$, Si substrate/SiN/Ta$_2$O$_5$, or Si substrate/SiN/TiO$_2$.

20. The detection system according to claim 16 wherein the one or more probe molecules are independently selected from the group of non-polymeric small molecules, polypeptides or proteins, oligonucleotides, and combinations thereof.

21. The detection system according to claim 16 wherein the detector is an imaging array that captures an image of at least a substantial portion of the surface of the chip.

22. A method for sensing at least one target, the method comprising:
    providing a detection system, comprising:
        a flow cell comprising:
            first and second members that are secured together to define a substantially fluid-tight chamber having an inlet and an outlet, at least the second member being light transmissive;
            a chip comprising a substrate, one or more coating layers on the substrate, and one or more probe molecules tethered to the outermost coating layer, the chip being positioned with the outermost coating layer and the one or more probe molecules thereon exposed to aqueous fluid in the chamber and facing the second member, whereby light passing through the second member and aqueous fluid is reflected by the chip; and
            wherein the one or more probe molecules specifically bind to one or more target molecules;
        an aqueous sample source in fluid communication with the inlet of the flow cell;
        a light source that is positioned to illuminate the chip with s-polarized light; and
        a detector that is positioned to detect light reflected from the surface of the chip, wherein the one or more coating layers are suitably dimensioned and the angle of incidence of the illuminating s-polarized light is suitable to produce a condition of near perfect destructive interference in the absence of the one or more target molecules and a substantial change in s-polarized light reflectivity in the presence of the one or more target molecules;
    directing s-polarized light at the front and back surfaces of the coating on the chip in a manner effective to result in a condition of near perfect destructive interference;
    introducing an aqueous sample into the flow cell;
    measuring s-polarized light reflected from the chip; and
    providing an output identifying the at least one target based on the measured reflected light.

23. The method according to claim 22 wherein said measuring the reflected light further comprises capturing an image of at least a substantial portion of the surface of the chip.

24. The method according to claim 22 wherein the at least one target is selected from the group consisting of peptides, proteins, glycoproteins, peptidoglycans, carbohydrates, lipoproteins, a lipoteichoic acid, lipid A, phosphates, nucleic acids, pathogens, whole cells, organic compounds, and combinations thereof.

25. The method according to claim 22 further comprising:
    recovering the aqueous sample that passes from the outlet of the flow cell; and
    analyzing the recovered aqueous sample.

26. The method according to claim 22 further comprising:
    dissociating the at least one target bound to the one or more probe molecules during use of the detection system;
    recovering dissociated target; and
    analyzing the recovered target.

* * * * *